United States Patent [19]

Gallick-Whitaker

[11] Patent Number: 4,525,584

[45] Date of Patent: Jun. 25, 1985

[54] 4AR,8AS,9R-5,6-PERMISSIBLY SUBSTITUTED-9-HYDROXY-OCTAHYDRO-1H(AND 2H) PYRAZOLO[3,4-G]QUINOLINE

[75] Inventor: Nancy G. Gallick-Whitaker, Indianapolis, Ind.

[73] Assignee: Eli Lilly and Company, Indianapolis, Ind.

[21] Appl. No.: 637,355

[22] Filed: Aug. 3, 1984

[51] Int. Cl.$^3$ .................. C07D 471/00; C07H 17/00; A01N 43/42; A61K 31/47

[52] U.S. Cl. ........................................ 536/24; 546/84; 546/82

[58] Field of Search .................. 546/82, 84; 424/258; 536/24

[56] References Cited

U.S. PATENT DOCUMENTS

| 3,649,634 | 3/1972 | Fujimara et al. | 424/258 |
| 3,897,434 | 7/1975 | Katner et al. | 546/82 |
| 4,230,861 | 10/1980 | Kornfeld et al. | 546/82 |
| 4,468,401 | 8/1984 | Hahn | 546/82 |

Primary Examiner—Henry R. Jiles
Assistant Examiner—Ann Bucci
Attorney, Agent, or Firm—James L. Rowe; Arthur R. Whale

[57] ABSTRACT

4aR,8aS,9R-5-$C_{1-3}$ straight-chain alkyl (methyl, ethyl or n-propyl) or allyl-9-hydroxy-octahydro-1H(and 2H)-pyrazolo[3,4-g]quinolines useful as hypotensives.

4 Claims, No Drawings

4AR,8AS,9R-5,6-PERMISSIBLY SUBSTITUTED-9-HYDROXY-OCTAHYDRO-1H(AND 2H) PYRAZOLO[3,4-G]QUINOLINE

BACKGROUND OF THE INVENTION

Kornfeld and Bach, U.S. Pat. No. 4,198,415, disclose and claim trans-($\pm$)-5-permissibly substituted-4,4a,5,6,7,8,8a,9-octahydro-1H-pyrazolo-[3,4-g]quinolines and their tautomers, the corresponding 2H derivatives (I and II below), useful as dopamine D-2 agonists.

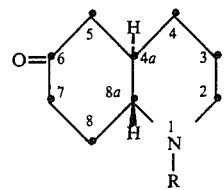

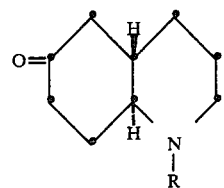

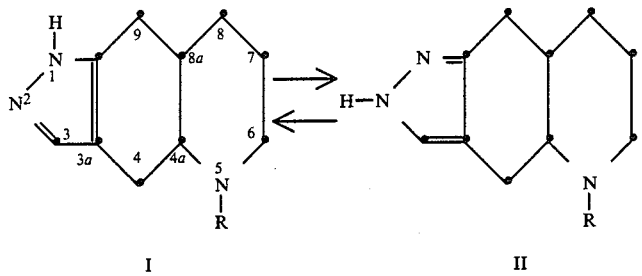

Each tautomeric trans-($\pm$) racemate consists of two enantiomers, the 4aR,8aR and 4aS,8aS derivatives. These four enantiomers are pictured below—Ia and Ib for the 1H tautomers; IIa and IIb for the 2H tautomers.

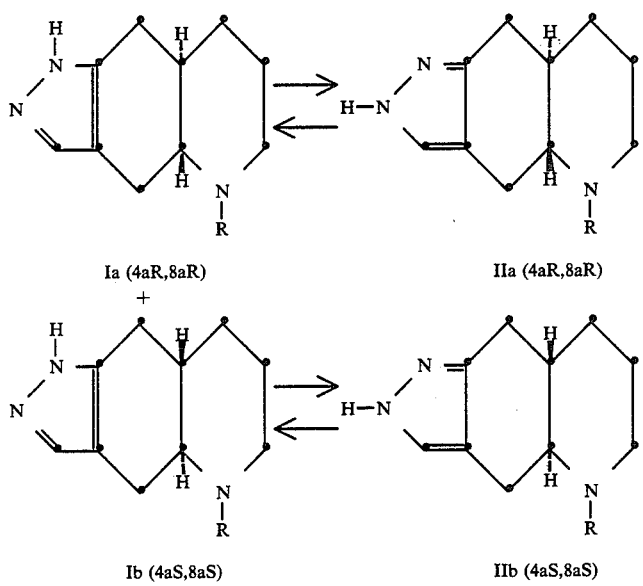

The copending application of Titus and Kornfeld, Ser. No. 439,238, filed 11/3/82, discloses a method of separating the tautomer pair I and II into their respective enantiomers (Ia and Ib or IIa and IIb) when R is n-propyl. Alternatively, the final tautomeric enantiomers can be prepared from an optically-active intermediate, a 4aR,8aR-1-$C_{1-3}$ straight-chain alkyl or allyl-6-oxodecahydroquinoline (III) or a 4aS,8aS enantiomer (IV). The copending application of Schaus and Booher, Ser. No. 639,107, also filed 11/3/82, separates trans-($\pm$)-1-$C_{1-3}$ straight-chain alkyl or allyl (specifically n-propyl)-6-oxodecahydroquinoline into these enantiomers where R is $C_{1-3}$ straight-chain alkyl or allyl.

Reaction of III with the dimethylacetal of dimethylformamide or with tris dimethylaminomethane forms a 7-dimethylaminomethylene derivative, reaction of which with $NH_2NH_2$ yields the tautomeric enantiomer, Ia$\rightleftarrows$IIa.

The tautomeric pair Ia$\rightleftarrows$IIa has been found to be useful in treating both hypertension and sexual dysfunction in mammals, see Hahn et al, *J.P.E.T*, 224, 206 (1982) and the copending application of Foreman, Ser. No. 518,906, filed 8/1/83.

The metabolism of the enantiomeric tautomers, Ia$\rightleftarrows$IIa, in mammals has not hitherto been disclosed nor have ring-oxygenated derivatives of trans-(±)-5-permissibly-substituted-4,4a,5,6,7,8,8a,9-octahydro-1H(and 2H)-pyrazolo[3,4-g]quinolines.

SUMMARY OF THE INVENTION

This invention provides 4aR,8aS,9R-5-$C_{1-3}$ straight-chain alkyl or allyl-6-permissibly-substituted-9-substituted-4,4a,5,6,7,8,8a,9-octahydro-1H-pyrazolo-[3,4-g]quinolines, formula Xa and its 2H tautomer, formula Xb, and pharmaceutically acceptable acid addition salts thereof

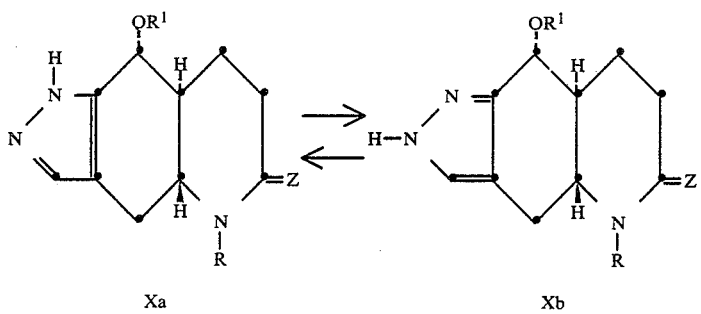

wherein R is methyl, ethyl, n-propyl or allyl, $R^1$ is H or D-glucuronyl, and Z is O or $H_2$ (a methylene group when taken with the carbon atom). Compounds according to Xa⇌Xb wherein Z is $H_2$ and $R^1$ is H are produced by enzymatic hydrolysis of the corresponding derivatives wherein $R^1$ is D-glucuronyl.

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, naphthalene-2-sulfonate and the like salts.

The tautomeric pair Xa⇌Xb is prepared by feeding a tautomeric pair according to Ia⇌IIa to a mammal—rat, mouse, dog or monkey—and isolating the corresponding 9-D-glucuronide or 6-oxo-9-hydroxy compound from urine collected during said feeding period. HPLC is employed to effect the separation of the desired metabolite from other co-produced metabolites. 4aR,8aS,9R-5-$C_{1-3}$ straight-chain alkyl or allyl-9-hydroxy-4,4a,5,6,7,8,8a,9-octahydro-1H(and 2H)-pyrazolo[3,4-g]quinoline is prepared by enzymatic hydrolysis (glucuronidase) of the 9-glucuronide derivative.

SPECIFIC EMBODIMENT OF THE INVENTION

A typical preparation of a compound according to Xa⇌Xb wherein R is n-propyl, Z is $H_2$ and $R^1$ is D-glucuronyl follows:

Dog urine was applied to a Diaion HP-20 column. The column was washed with 2 column volumes of water. Approximately 60% of the radioactivity was then eluted using methanol/water (2 column volumes) mixtures in a 10% incremental gradient from 10–50% methanol in water. The remaining radioactivity (40%) was eluted with 5 column volumes of methanol. Fractions of the column eluate were assayed using the following HPLC system—100% $H_2O$, 5 min; 0–90% MeOH, 35 min; 90% MeOH, 10% $H_2O$, pH=7 (2 millimolar ammonium phosphate buffer), 15 min; (Column: Alltech C8, 10μ).

Fractions (40–50% methanol in $H_2O$) containing maximal amounts of the D-glucuronide of 4aR,8aS,9R-5-propyl-9-hydroxy-4,4a,5,6,7,8,8a,9-1H(and 2H)-pyrazolo[3,4-g]quinoline were combined. The radioactivity in the residue that resulted upon evaporation of the combined fractions was dissolved in a minimal amount of water. Ethyl acetate extraction of the aqueous solution (at pH 3 and 10) reduced background substances, leaving the radioactivity in the aqueous layer. The pH of the aqueous layer was neutralized and the solution was injected onto the following HPLC system 100% $H_2O$, 5 min; 0–100% MeOH, 37.5 min.; Whatman Partial 5,0DS-3, RAC. The column eluate corresponding to the D-glucuronide of 4aR,8aS,9R-5-n-propyl-9-hydroxy-4,4a,5,6,7,8,8a,9-octahydro-1H(and 2H)-pyrazolo[3,4-g]quinoline was collected, and the product isolated by evaporation of the solvent. Final purification was achieved by precipitation of the glucuronide from a 1:1 mixture of methanol and absolute ethanol.

The 9-D-glucuronyl derivative was converted to the 9-hydroxy derivative by the following procedure. A 500 mcg fraction of purified 9-D-glucuronide was dissolved in 0.1M phosphate buffer (pH=7.0) containing 5000 units of β-glucuronidase (Sigma, bacterial type VII). The solution was incubated for 24 hr at 37° C. The incubation mixture was injected onto the above HPLC system, the column eluate corresponding to 4aR,8aS,9R-5-n-propyl-9-hydroxy-4,4a,5,6,7,8,8a,9-octahydro-1H(and 2H)-pyrazolo[3,4-g]quinoline collected and the compound obtained by evaporation of the solvent.

The above products had the following physical characteristics: for the D-glucuronide of 4aR,8aS,9R-5-n-propyl-9-hydroxy-4,4a,5,6,7,8,8a,9-octahydro-1H(and 2H)-pyrazolo[3,4-g]quinoline.

Mass spectrum (fast atom bombardment); 412, (molecular ion), 394, 218,207.

Mass spectrum (fast atom bombardment of molecular ion 412); 394, 328,218.

Infrared spectrum; 1610, broad band at 3200–3600 cm$^{-1}$.

NMR (D$_2$O): δ at 1.02, 1.57, 1.83, 2.13, 2.28, 2.54, 2.72, 3.18, 3.36, 3.43, 3.45, 3.53, 3.61, 3.65, 3.65, 4.10, 4.83.

For 4aR,8aS,9R-5-n-propyl-9-hydroxy-4,4a,5,6,7,8-,8a,9-octahydro-1H(and 2H)-pyrazolo[3,4-g]quinoline.

Mass spectrum (high resolution electron impact): ions at 235 (molecular ion), 218, 206, 125, 109, 96.

NMR (D$_2$O): δ at 0.92, 1.28, 1.63, 1.70, 1.89, 2.36, 2.42, 2.56, 2.71, 2.86, 3.13, 3.23, 4.51.

4aR,8aS,9R-5-n-propyl-9-hydroxy-4,4a,5,6,7,8,8a,9-octahydro-1H(and 2H)-pyrazolo[3,4-g]quinoline can also be prepared by LiAlH$_4$ reduction of 4aR,8aS,9R-5-n-propyl-6-oxo-9-hydroxy-4,4a,5,6,7,8,8a,9-octahydro-1H- (and 2H)-pyrazolo[3,4-g]quinoline. This latter compound is also a metabolite where R is n-propyl of Ia⇌IIa when fed to mammals. Its isolation follows:

Urine from monkeys given a 2 mg/kg (or 20 mg/kg) nasogastric dose of $^{14}$C-4aR,8aR-5-n-propyl-4,4a,5,6,7,8,8a,9-octahydro-1H(and 2H)-pyrazolo[3,4-g]-quinoline (Ia⇌IIa where R is n-propyl) was applied to a Diaion HP-20 column. The column was washed with water until radioactivity was detected in the eluate. The radioactivity (ave. 94%) was then eluted with methanol. Radioactivity in the residue that resulted upon evaporation of the methanolic fraction was then selectively dissolved in a minimal volume of various organic solvents (methanol, ethanol, and ethanol, ethyl acetate (2:1)). This treatment caused precipitation of endogenous substances and allowed the radioactivity to be concentrated in a small volume of methanol suitable for thin-layer chromatography on silica gel plates [chloroform/methanol/15N ammonium hydroxide (45:50:5)]. Autoradiography of the developed TLC plates revealed five broad bands. Regions corresponding to the bands were scraped from the plates, the radioactive metabolites were eluted from the scrapings with methanol, and the eluates evaporated to dryness under reduced pressure.

The radioactive material associated with TLC band (R$_f$=0.58–0.85) was dissolved in 0.01N aqueous NaOH, and the desired radioactive metabolite was extracted with ethyl acetate. The ethyl acetate extract was washed with 0.01N HCl. The pH of the acidic aqueous layer was adjusted to neutrality using 1N aqueous NaOH. Injection of the aqueous extract into the following HPLC system yielded 4aR,8aS,9R-5-n-propyl-6-oxo-9-hydroxy-4,4a,5,6,7,8,8a,9-octahydro-1H(and 2H)-pyrazolo[3,4-g]quinoline: 100% water, 5 min; 0–100% methanol, 37.5 min; (Whatman Partisil 5, ODS-3, RAC column). This procedure gave the tautomeric pair 4aR,8aS,9R-5-n-propyl-6-oxo-9-hydroxy-4,4a,5,6,7,8,8a,9-octahydro-1H(and 2H)-pyrazolo[3,4-g]quinoline. The product was further purified by HPLC using a different solvent system but the same column: 40% MeOH, 60% H$_2$O; 12 min.

The compound thus purified had the following physical characteristics:

Mass Spectrum (field desorption); molecular ion at 249; (High resolution electron impact) 249 (molecular ion), 231, 220, 140, 110.

Infrared spectrum (CHCl$_3$): 1618 cm$^{-1}$ (lactam carbonyl).

NMR (CDCl$_3$): δ at 1.86 (H-8a axial), 2.43 (H-4 axial), 3.22 (H-4 equatorial), 3.39 (H-4a axial), 4.60 (H-9 axial).

4aR,8aS,9R-5-n-propyl-9-hydroxy-4,4a,5,6,7,8,8a,9-octahydro-1H(and 2H)-pyrazolo[3,4-g]quinoline has hypotensive activity, as demonstrated by the following experiment.

Adult male spontaneously hypertensive rats (SHR) (Taconic Farms, Germantown, N.Y.), weighing approximately 300 g were anesthetized with pentobarbital sodium (60 mg/kg/i.p.). The trachea was cannulated and the SHR respired room air. Pulsatile arterial blood pressure was measured from a cannulated carotid artery using a Statham transducer (P23 ID). Mean arterial blood pressure was calculated as diastolic blood pressure plus ⅓ pulse pressure. Cardiac rate was monitored by a cardiotachometer which was triggered by the systolic pressure pulse. Drug solutions were administered i.v. through a catheter placed in a femoral vein. Arterial blood pressure and cardiac rate were recorded on a multichannel oscillograph (Beckman, Model R511A). Fifteen minutes were allowed to elapse following surgery for equilibration of the preparation.

Table 1 which follows gives the results of this experiment for 4aR,8aS,9R-5-n-propyl-9-hydroxy-4,4a,5,6,7,8,8a,9-octahydro-1H(and 2H)-pyrazolo[3,4-g]-quinoline. The drug was administered i.v. to groups of four SHR at a series of dose levels.

TABLE 1

Percent Changes in Blood Pressure and Heart Rate[a]

| Dose mg/kg | Mean Arterial[b] Blood Pressure | Cardiac Rate |
|---|---|---|
| 1 | −9.4 ± 8.3 | −5.4 ± 4.1 |
| 10 | −8.2 ± 1.5 | −3.6 ± 0.7 |
| 100 | −23.2 ± 2.7[c] | −9.0 ± 1.9 |
| 500 | −11.9 ± 3.2[c] | −9.6 ± 1.0 |

[a]The initial baseline mean arterial blood pressure was 181 ± 8 mm Hg, and the mean cardiac rate was 359 ± 11 beats per minute.
[b]Mean response ± standard error of 4 SHR.
[c]Response of approximately 10 minutes duration.

For treating hypertension in mammals, the above base or a pharmaceutically-acceptable salt thereof formed with a non-toxic acid, preferably the dihydrochloride salt, is administered parenterally or orally. For oral administration the drug is mixed with one or more pharmaceutical diluents and/or excipients, and the mixture loaded into telescoping gelatin capsules such that each capsule contains a hypotensive dose of the drug.

Pharmaceutically-acceptable salts of the tautomeric bases represented of Xa⇌Xb above when R$^1$ is H, Z is H$_2$ and R is methyl, ethyl, n-propyl or allyl can be prepared by mixing a solution of the base in ether, adding an etheral solution of the non-toxic acid, and isolating the insoluble salt by filtration. Alternatively, alcoholic solutions, each containing an equivalent of the base and an equivalent of the acid, are mixed and the alcohol soluble salt is isolated by evaporation of the solvent. The preferred dihydrochloride salt is prepared by saturating an ethereal solution of the base with dry gaseous HCl.

I claim:
1. Tautomeric pairs of the formulas

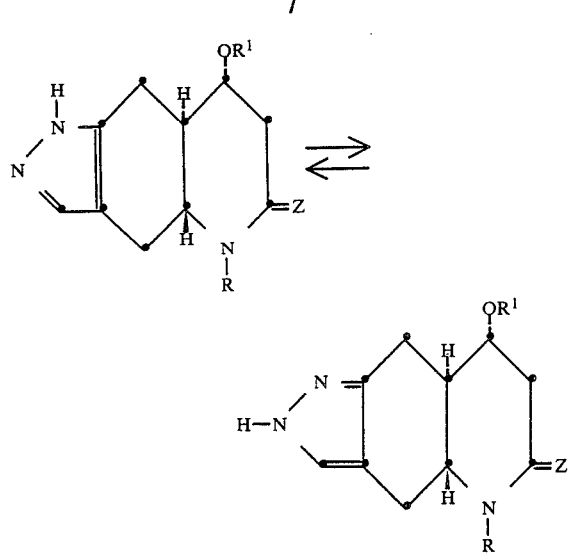

wherein R is methyl, ethyl, allyl, or n-propyl, $R^1$ is H or D-glucuronyl, and Z is O or $H_2$.

2. A tautomeric pair according to claim 1, said pair being 4aR,8aS,9R-5-n-propyl-9-hydroxy-4,4a,5,6,7,8,8a,9-octahydro-1H(and 2H)-pyrazolo[3,4-g]quinoline.

3. A tautomeric pair according to claim 1, said pair being the D-glucuronide of 4aR,8aS,9R-5-n-propyl-9-hydroxy-4,4a,5,6,7,8,8a,9-octahydro-1H(and 2H)-pyrazolo[3,4-g]quinoline.

4. A tautomeric pair according to claim 1, said pair being 4aR,8aS,9R-5-n-propyl-6-oxo-9-hydroxy-4,4a,6,7,8,8a,9-octahydro-1H(and 2H)-pyrazolo[3,4-g]quinoline.

* * * * *